(12) United States Patent
Hakamata

(10) Patent No.: US 6,716,162 B2
(45) Date of Patent: Apr. 6, 2004

(54) FLUORESCENT ENDOSCOPE APPARATUS

(75) Inventor: Kazuo Hakamata, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 234 days.

(21) Appl. No.: 09/840,457

(22) Filed: Apr. 24, 2001

(65) Prior Publication Data

US 2003/0045777 A1 Mar. 6, 2003

(30) Foreign Application Priority Data

Apr. 24, 2000 (JP) ........................................ 2000-122159

(51) Int. Cl.[7] ................................................ A61B 1/06
(52) U.S. Cl. ........................ 600/181; 600/160; 600/476; 359/361
(58) Field of Search ................................ 600/160, 178, 600/476, 181; 359/656, 722, 723, 350, 361, 355, 359

(56) References Cited

U.S. PATENT DOCUMENTS

| | | | | |
|---|---|---|---|---|
| 5,481,401 A | * | 1/1996 | Kita et al. ................... | 359/353 |
| 5,658,070 A | * | 8/1997 | Rowe et al. ................ | 362/283 |
| 5,683,804 A | * | 11/1997 | Nagashima et al. ........ | 428/336 |
| 5,696,564 A | * | 12/1997 | Hatakeyama ............... | 348/756 |
| 5,861,996 A | * | 1/1999 | Yamaguchi ................. | 359/656 |
| 5,920,432 A | * | 7/1999 | Suenaga et al. ............ | 359/656 |
| 6,219,189 B1 | * | 4/2001 | Tomimatsu et al. ........ | 359/659 |
| 6,471,636 B1 | * | 10/2002 | Sano et al. ................. | 600/109 |

FOREIGN PATENT DOCUMENTS

| | | | |
|---|---|---|---|
| DE | 198 49 777 A1 | 4/1999 | |
| EP | 0 068 404 A1 | 1/1983 | |
| JP | 10-254001 | 9/1998 | ............ G02F/1/37 |
| WO | WO 98/58252 A1 | 12/1998 | |

* cited by examiner

*Primary Examiner*—John P. Leubecker
(74) *Attorney, Agent, or Firm*—Sughrue Mion, PLLC

(57) ABSTRACT

A fluorescent endoscope apparatus in which the fluorescent light, which becomes noise, emitted from the photographic element propagating the autofluorescent light emitted from a living-tissue subject is reduced, and by which it is possible to clearly distinguish between normal and diseased tissues. The fluorescent endoscope apparatus has a stimulating light projecting unit for irradiating a living-tissue subject with stimulating light, and an optical element for propagating the autofluorescent light emitted from the living tissue subject that has been irradiated by stimulating light. It also has a photographing element, which is formed of the optical element, for photographing the autofluorescent light emitted by the living tissue subject irradiated by the stimulating light. The optical element is structured so as to satisfy the condition expressed by the formula: the strength of the autofluorescent light of normal tissue $\geq$ the strength of the autofluorescent light of the optical element $\times 10^4$.

3 Claims, 6 Drawing Sheets

FLUORESCENT ENDOSCOPE APPARATUS

BACKGROUND OF THE INVENTION

1. Field of the Invention

The present invention relates in general to a fluorescent endoscope apparatus for photographing as an image the autofluorescent light emitted from a living-tissue subject, representing the state of the tissues of the living-tissue subject, upon irradiation thereof by stimulating light.

2. Description of the Related Art

Researchers have long been researching fluorescent endoscope apparatuses for use in detecting the extremely faint fluorescent light emitted from a living-tissue subject irradiated by stimulating light, which can then be analyzed to distinguish the change of state in tissues accompanying various diseases.

For example, in in-vitro cancer diagnosis studies employing autofluorescence, by use of stimulating light having several specified wavelengths of light from within the wide spectrum covering the 330–450 nm range, it has been shown that it is possible to distinguish between normal and diseased tissues using this technique.

When light having such short wavelengths, from within the range spanning from the UV to the visible spectra, is employed as stimulating light, fluorescent light is emitted from the optical element forming the stimulating light projecting portion when the stimulating light is propagated therethrough. Also, the shorter the wavelength of the stimulating light, the higher the strength of the fluorescent light emitted from the optical element. Because of this, there are cases in which a non-fluorescent material such as silica, etc., which emits less fluorescent light when the stimulating light is transmitted therethrough, is used for forming the optical element forming the stimulating light projecting portion.

However, it was found that when a non-fluorescent material such as silica is used to form the optical element as a measure to reduced the strength of the fluorescent light emitted therefrom, fluorescent light containing the same wavelengths of the autofluorescent light is also emitted from the photographing portion photographing the image formed by the autofluorescent light (hereinafter also referred to as an autofluorescent image Zj) emitted by a living-tissue subject that has been irradiated by stimulating light. That is to say, the light reflected from the living-tissue subject irradiated by stimulating light enters the photographing portion, and by entry of this reflected stimulating light into the photographing portion, the constituent material of the optical element propagating the autofluorescent light contained within the photographing portion (for example, the components contained in multi-component glass, or the organic material component contained in colored fiber, etc.) have been found to emit fluorescent light upon exposure to stimulating light. Therefore, the fluorescent light emitted from this optical element is mixed, as noise, with the autofluorescent light entering the photographing portion, and as a result, the are instances in which an autofluorescent image containing much noise is photographed.

For example, there are studies in which, using a fiber-optic endoscope, in which the autofluorescent light is propagated by an image fiber, the strength of the fluorescent light emitted by the objective lens and image fiber has been found to be 0.8–0.9 times the value of the autofluorescent light emitted from normal tissue of a living-tissue subject. Furthermore, there are studies in which, irradiated by the same strength of stimulating light, the autofluorescent light emitted by a diseased tissue that should be the object of observation, which is 1/10 of that of normal tissue, becomes buried in the fluorescent light, which becomes noise, produced by a forementioned objective lens and image fiber, and the diseased tissue has been spuriously diagnosed as a negative portion.

In addition, the normal observation range of a fluorescent endoscope apparatus is from a close point at a distance of 5 mm from the forward end of the endoscope portion to a far-point at a distance of 55 mm from the forward end of the endoscope portion. When the autofluorescent light emitted from the live-tissue subject located 55 mm from the forward end of the endoscope portion, which has been irradiated by the stimulating light Le projected from the forward end of the endoscope portion, is received at the photographing portion after being propagated thereto through the optical element, a portion of the stimulating light projected from the forward end of the endoscope portion toward the living-tissue subject located at a distance of 5 mm away from the forward end of the endoscope portion is reflected, and when this reflected stimulating light Lf is propagated within the optical element, the fluorescent light emitted by the optical element, which becomes noise, is received by the photographing portion together with aforementioned autofluorescent light, and even under the condition of the lowest possible S/N ratio enabling observation (that is, the condition of the observational limit), it is desirable that the diseased tissue and the normal tissue can be clearly distinguished.

SUMMARY OF THE INVENTION

The present invention has been developed in consideration of the circumstances described above, and it is a primary objective of the present invention to provide a fluorescent endoscope apparatus in which the fluorescent light, which becomes noise, emitted from the photographic element propagating the autofluorescent light emitted from a living-tissue subject is reduced, and by use of which it is possible to clearly distinguish between normal and diseased tissues.

The fluorescent endoscope apparatus according to the present invention comprises a stimulating light projecting means for irradiating a living-tissue subject with stimulating light, and a photographing means formed of an optical element for transferring the autofluorescent light emitted from the live-subject tissue upon irradiation thereof by stimulating light and a photographing element for photographing the autofluorescent light transferred thereto by said optical element, wherein said optical element is constructed so that the relationship of the normal-tissue fluorescent light of a strength K, which is the strength of the autofluorescent light emitted from the normal tissue of the live-tissue subject that has been transferred through said optical element and received by the photographing element, to the optical-element fluorescent light of a strength B, which is the strength of the fluorescent light emitted by said optical element when the reflected stimulating light reflected from the living tissue subject upon irradiation thereof by stimulating light is propagated through said optical element, satisfies the condition expressed by the formula: $K \geq B \times 10^4$.

Note that normal-tissue fluorescent light of a strength K and optical-element fluorescent light of a strength B are measured values as described below.

As shown in FIG. 1A, the autofluorescent light Lj emitted by a living-tissue subject 1, of which all regions are normal tissue, upon irradiation thereof by stimulating light Le is passed through an optical element 2 formed of a stimulating light cutoff filter 2a that cuts off substantially 100 percent of the stimulating light and a focusing optical system 2b, and is received by a photographing element 3. On the other hand, the stimulating light reflected by living-tissue subject 1 upon irradiation thereof by stimulating light, reflected stimulating light Lh, is substantially 100 percent cutoff by cutoff filter 2a before entering focusing optical system 2b. At this point, the unit per area strength of autofluorescent light Lj received by photographing element 3 is strength K.

As shown in FIG. 1B, the positions of the stimulating light cutoff filter 2a and the focusing optical system 2b forming optical element 2 are switched and stimulating light cutoff filter 2a is disposed between photographing element 3 and focusing optical system 2b, and when the aforementioned living-tissue subject 1 is irradiated by stimulating light Le, the autofluorescent light Lj emitted by said living tissue subject 1 passes through optical element 2 and is received by photographing element 3. On the other hand, when the reflected stimulating light Lh reflected by said living-tissue subject upon irradiation thereof by stimulating light Le enters focusing optical system 2b, the constituent material forming focusing optical system 2b is stimulated by the reflected stimulating light Lh and emits fluorescent light Lk. Afterwards, reflected stimulating light Lh passes through focusing optical system 2b and before entering photographing element 3 is substantially 100 percent cutoff by stimulating light cutoff filter 2a, however, because the fluorescent light Lk emitted by said focusing optical system 2b contains light of the same wavelength range as that of the autofluorescent light Lj, said fluorescent light Lk passes through stimulating light cutoff filter 2a and is received by photographing element 3.

Here, if the unit per area strength of the product of the autofluorescent light Lj and the fluorescent light Lk received by photographing element 3 are designated as multiplied fluorescent light strength X, the value resulting from subtracting normal-tissue fluorescent light strength K from multiplied fluorescent light strength X (multiplied fluorescent light strength X—normal-tissue fluorescent light of a strength K) becomes the optical element fluorescent light strength B, which represents the unit per area strength of the fluorescent light Lk emitted by optical element 2 and received by photographing element 3.

The optical element is provided with a stimulating light cutoff filter for selectively cutting off the stimulating light. The stimulating light cutoff filter can be provided as a panel of optical glass on which a multiple-layer dielectric film has been formed.

It is preferable that at least one of aforementioned optical element components through which the autofluorescent light is passed and which is disposed between the aforementioned a multiple-layer dielectric film and the living-tissue subject has properties satisfying the condition expressed by the following formulae:

$$\lambda_{ex} > \lambda_{80} + (8/15) \times (\lambda_{80} - \lambda_{05})$$

Where:

$\lambda_{ex}$=the wavelength of the stimulating light $\lambda_{80}$=the wavelength at which the optical element exhibits the transmittance of 80%

$\lambda_{05}$=the wavelength at which the optical element exhibits the transmittance of 5%

It is preferable that the stimulating light have a wavelength of 445 nm or smaller.

A GaN semiconductor laser, a mercury lamp, a xenon lamp, or a metal halide lamp can be employed as the stimulating light source.

Note that the referent of the aforementioned optical element includes all elements with the capability of passing stimulating light and reflecting stimulating light, and includes not only the lenses, prisms, etc., but also the mirror tubing and other support members, etc. used to support these components, as well as the adhesives, etc. used to join together or secure said components and support members, etc. in place.

According to the fluorescent endoscope apparatus of the present invention, upon photographing the autofluorescent light emitted by a living tissue subject upon irradiation thereof by stimulating light, because the optical element has been constructed so that the relationship between normal-tissue fluorescent light of a strength K and optical element fluorescent light strength B satisfies the condition expressed by the formula: $K \geq B \times 10^4$, even under aforementioned observational limit condition, which is the condition among the observation conditions in which the most noise is contained, the difference between normal tissue and diseased tissue can be clearly distinguished.

For example, as shown in FIG. 2, stimulating light Le is projected from end face 40a of endoscope forward end portion 40, and the value of the far-point autofluorescent light strength Fj, which is the unit per area strength of the autofluorescent light Lj emitted by the normal tissue of a living-tissue subject located at a far-point P1 at a distance of 50 mm from end face 40a of and which has been passed through optical element 2 and received by photographing element 3, is 100 (Fj=100). On the other hand, the value of the far-point optical element fluorescent light strength Fk, which is the unit per area strength of the fluorescent light Lk emitted by the constituent material of optical element 2 upon stimulation thereof by the passing therethrough of the reflected stimulating light Lh reflected by living-tissue subject 1 located at a far-point P2 at a distance of 50 mm from end face 40a of and which has been received by photographing element 3, is less than $1/1 \times 10^4$ that of Fj; $Fk \leq 0.01$. The value of the close-point optical element fluorescent light strength Ck, which is the unit per area strength of the fluorescent light Lk emitted by the constituent material of optical element 2 upon stimulation thereof by the passing therethrough of the reflected stimulating light Lh reflected by living-tissue subject 1 located at a close-point P3 at a distance of 5 mm from end face 40a of and which has been received by photographing element 3, is substantially 100 times that of the value of the far-point optical element fluorescent light strength Fk for far-point P2 (because it is 1/10 the distance to the position of the living-tissue subject reflecting the stimulating light Le projected from end face 40a is, close-point optical element fluorescent light strength Ck is 100 times that of reflected stimulating light Lh); close-point optical element fluorescent light strength Ck is 1 or less (herein, the substantial reflectance of the stimulating light Le reflected by the living-tissue is supposed to be 1).

Accordingly, under the condition of the observational limit, in which the autofluorescent light emitted by the living-tissue subject to become the object of observation is located at a far-point is mixed with the fluorescent light, which becomes noise, emitted by the optical element when the reflected stimulating light is propagated therethrough, for cases in which said living-tissue subject is a normal tissue, the strength ratio of the autofluorescent light Lj emitted from said living-tissue subject to the fluorescent light Lk, which becomes noise, emitted from optical element 2, Ck/Fj is less than $1/100$, and for cases in which the said living-tissue subject is diseased tissue, because the strength ratio of the autofluorescent light Lj emitted from said living-tissue subject to the fluorescent light Lk, which becomes noise, emitted from optical element 2 is less than $1/10$, the autofluorescent light representing the living-tissue subject that is the object of observation does not become buried in the fluorescent light, which becomes noise, emitted by the optical element, and observation can be performed wherein the difference between normal and diseased tissue can be clearly distinguished.

In addition, the optical element is provided with a stimulating light cutoff filter for selectively cutting off the stimulating light, and the aforementioned stimulating light cutoff filter is provided as a panel of optical glass on which a multiple-layer dielectric film has been formed, such that the apparatus can be provided having a better configuration.

Also, if at least one of the aforementioned optical element components through which the autofluorescent light is passed and which is disposed between the aforementioned multiple-layer dielectric film and the living-tissue subject has properties satisfying the condition expressed by the formulae listed below, the fluorescent light emitted by the optical element, which becomes noise, can be more precisely controlled:

$$\lambda_{ex} > \lambda_{80} + (8/15) \times (\lambda_{80} - \lambda_{05})$$

Where:

$\lambda_{ex}$=the wavelength of the stimulating light $\lambda_{80}$=the wavelength at which the optical element exhibits the transmittance of 80%

$\lambda_{05}$=the wavelength at which the optical element exhibits the transmittance of 5%

If the wavelength of the stimulating light is 445 nm or smaller, the autofluorescent light emitted from a living-tissue subject upon exposure thereto can be made to be emitted more precisely.

If the light source is a GaN semiconductor laser, a mercury lamp, a xenon lamp, or a metal halide lamp, stimulating light having a wavelength of 445 nm or smaller can be more easily obtained.

DESCRIPTION OF THE PREFERRED EMBODIMENTS

Hereinafter, the preferred embodiments of the present invention will be explained with reference to the drawings.

Figure 1A:
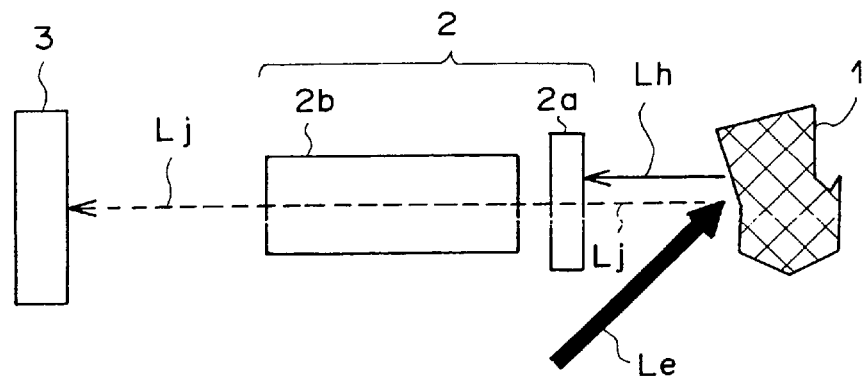
FIGS. 1A and 1B are schematic drawings showing the methods for obtaining the value of normal-tissue fluorescent light strength K and optical element fluorescent light strength B, respectively.
Figure 1B:
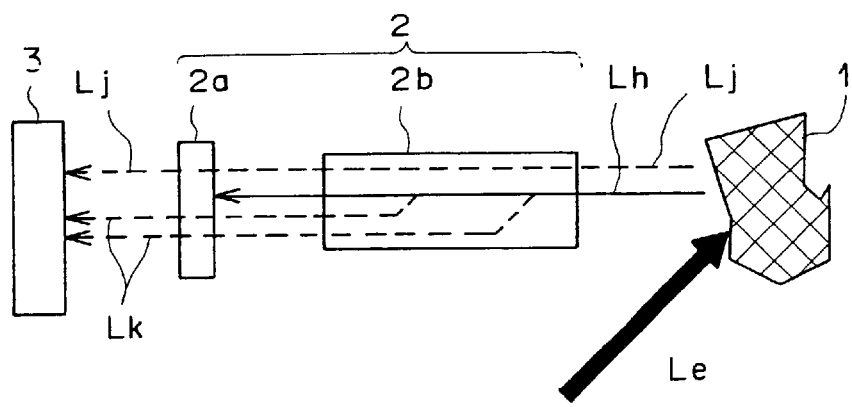
Figure 2:
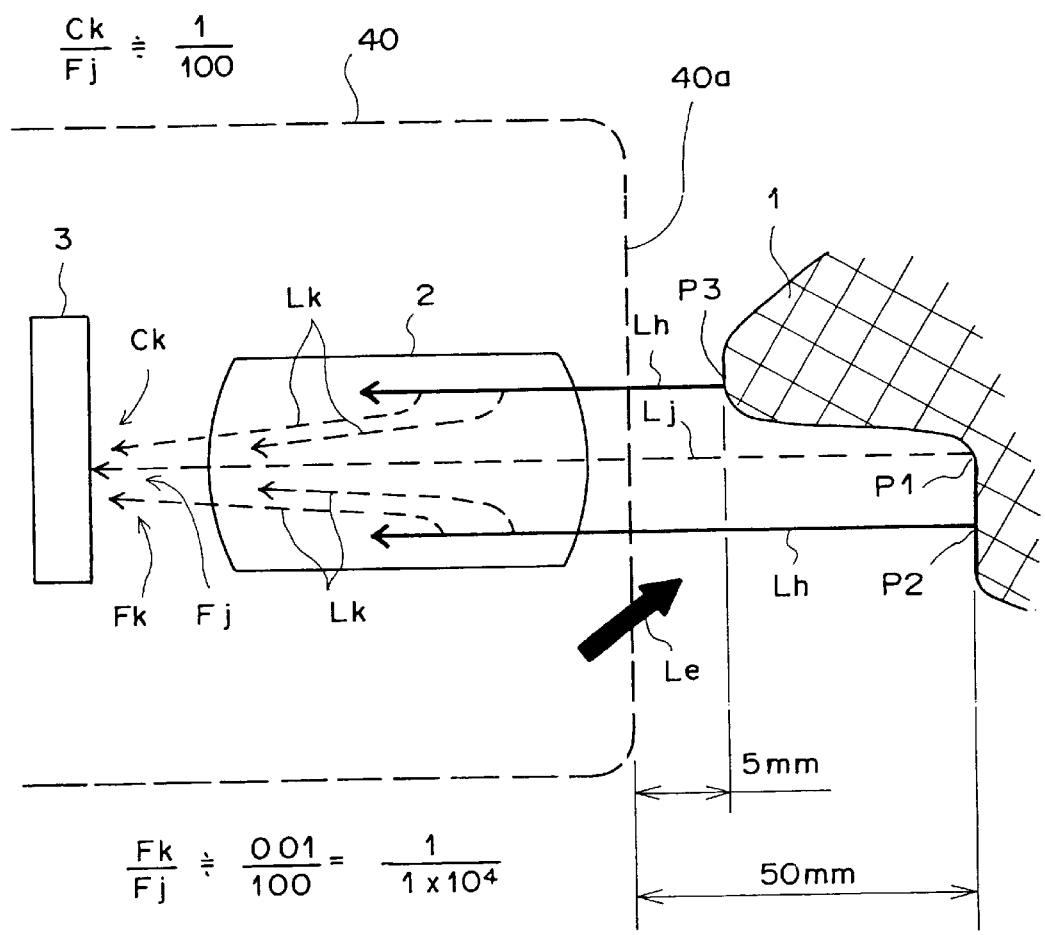
FIG. 2 is schematic drawing of the strength ratios of the autofluorescent light and the fluorescent light mixed therewith as noise.
Figure 3:
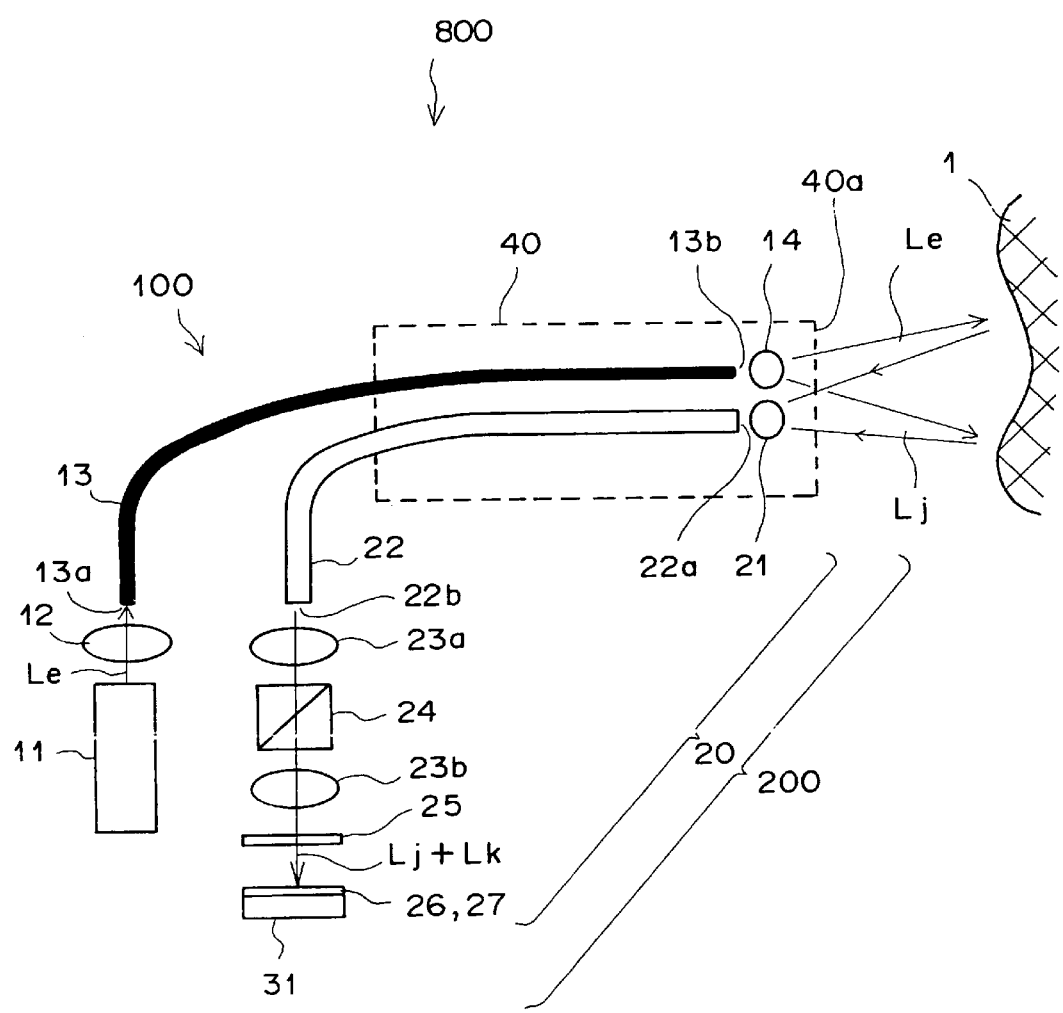
FIG. 3 is a schematic drawing of the configuration of a fiber-optic endoscope according to the first embodiment of the present invention.

FIG. 3 is a schematic drawing of the configuration of a first embodiment of a fiber-optic endoscope apparatus 800 implementing the present invention.

The fiber-optic endoscope apparatus 800 according to the embodiment comprises a stimulating light projecting portion 100 for irradiating living-tissue subject 1 with stimulating light Le, and a photographing portion 200 formed of an optical element 20 for propagating the autofluorescent light Lj emitted from the living-tissue subject irradiated by stimulating light Le and a photographing element 31 for photographing the autofluorescent light Lj propagated thereto by optical element 20.

Stimulating light projecting portion 100 is provided with a GaN semiconductor laser, a mercury lamp, a xenon lamp, or a metal halide lamp, etc., as stimulating light source 11 for emitting stimulating light Le (stimulating light wavelength $\lambda_{ex}$=410 nm), a condensing lens 12 for condensing the stimulating light emitted from stimulating light source 11, and a projecting lens 14 for irradiating a living-tissue subject 1 with the stimulating light Le which has been condensed by condensing lens 12, propagated to the output face 13b from input face 13a of light guide 13 and output therefrom. Note that the wavelength of stimulating light Le does not necessarily have to be 410 nm, however, it is preferable that it be 445 nm or smaller.

Optical element 20 is provided with an objective lens 21 for focusing the autofluorescent light Lj emitted from living-tissue subject 1 in the wavelength range covering the 35–700 nm spectra, which enters optical element 20, on the input face 22a of an image fiber 22, described below, as an autofluorescent image Zj representing the state of the tissue of living-tissue subject 1, an image fiber 22 for propagating the autofluorescent image Zj focused on input face 22a to the output face 22b thereof, relay lenses 23a and 23b for focusing the autofluorescent image Zj propagated to output face 22b on the light-receiving face of photographing element 31, a dichroic mirror 24 disposed between relay lens 23a and relay lens 23b for splitting light by allowing certain specified frequencies of light to pass and reflecting others, a stimulating light cutoff filter disposed between relay lens 23b and photographing element 31 for cutting of light having a wavelength of 430 nm, that is, a stimulating light cutoff filter, which is formed of an optical glass panel and the multi-layer dielectric film formed thereon, for selectively cutting off the stimulating light Le, and a micro lens array 26, which is formed of organic material, for condensing light entering the photographing element 31 onto each of the light receiving pixels thereof and a mosaic filter 27, which is formed of organic material, for splitting the light received on each light-receiving pixel of photographing element 31 into specific frequencies, wherein the micro lens array 26 is mounted on photographing elements 31 in an on-chip manner.

Therefore, the material used to form the optical element 20 is selected so that the relationship of the average strength of the autofluorescent light Fj emitted by the normal tissue of living-tissue subject 1 upon irradiation thereof by stimulating light Le and which has been passed through optical element 20 and received by photographing element 31, that is normal tissue fluorescent light strength K, to the average strength of the fluorescent light emitted by the constituent material of optical element 20 upon stimulation thereof by the reflected stimulating light Lf reflected by the living-tissue subject caused when said reflected stimulating light Lf passes therethrough, that is optical element fluorescent light strength B satisfied the condition expressed by the formula: $K \geq B \times 10^4$.

Note that the material to be used for forming the optical element through which the autofluorescent light passes can be selected from among materials having properties such as those described below. Degree of coloration is used to indicate the properties of optical element (glass) materials, and indicate wavelengths at which the absorption rate of these degrees of coloration expands extremely rapidly. Based on the degree of coloration, it can be estimated whether or not fluorescent light is emitted by the optical element upon irradiation thereof by stimulating light. For cases in which an optical system for transmitting autofluorescent light, which comprises a plurality of optical members through which autofluorescent light is passed, is used, among this plurality of optical members, at least with respect to the optical element, whose effect on the transparency characteristics of the overall of the optical system is large (that is, greatly reduces the rate of the passage of light therethrough), it is preferable that whether fluorescent light will be produced or not upon irradiation of said optical element by stimulating light be confirmed based on the degree of coloration.

Next, the degrees of coloration will be explained. As for normal glass, no light from the long wavelength side of the wavelength range are recognized to be absorbed by the absorption edge, and by use of wavelength $\lambda_{80}$, which represents 80% of the transmittance obtained when the splitting transmittance of the glass was measured and wavelength $\lambda_{05}$, which represents 5% of the transmittance obtained when the splitting transmittance of the glass was measured, those splitting transmittance characteristics can easily be shown, and using these two wavelengths, $\lambda_{80}$ and $\lambda_{05}$, the degree of coloration can be determined. More specifically, utilizing glass polished to a thickness of 10 mm±0.1 mm, the splitting transmittance of the wavelength range spanning from 280 nm to 700 nm (including light loss due to reflection) is measured, and the wavelengths registering a splitting transmittance of 5% and 80%, which are represented in 10 nm units, are the degrees of coloration: For example, the glass degree of coloration ratios of a wavelength of 398 nm, which represents the transparency ratio of 80%, and a wavelength of 362 nm, which represents the transparency ratio of 5%, are represented as 40/36.

Figure 6:
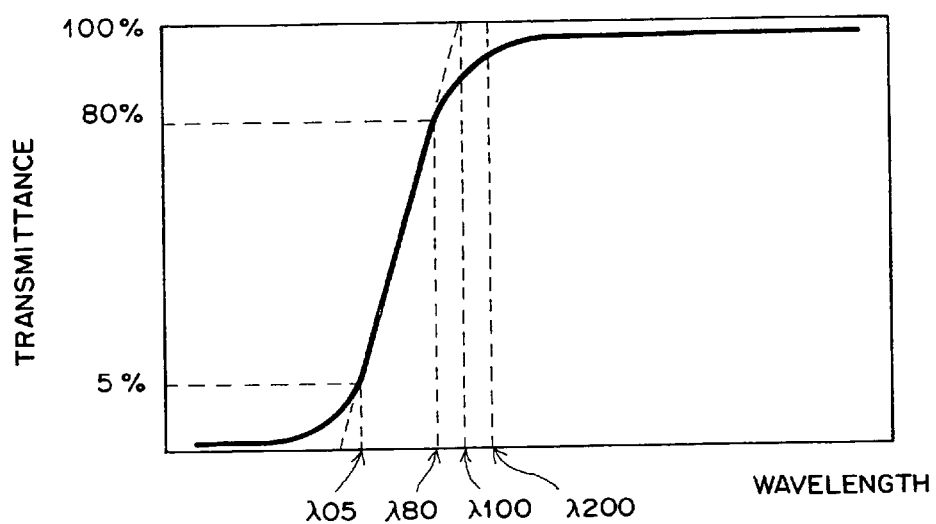
FIG. 6 shows the method for estimating whether or not fluorescent light will be emitted or not.

Next, with reference to FIG. 6 and utilizing the values of the wavelengths $\lambda_{80}$ and $\lambda_{05}$, the method of estimating whether or not fluorescent light will be emitted from the glass of an optical element will be shown. First, a wavelength $\lambda_{100}$, which is the wavelength at which the transparency ratio of the glass is 100%, is obtained of $\lambda_{80}$ and $\lambda_{05}$ as follows:

$$\lambda_{100} = (4/15) \times (\lambda_{80} - \lambda_{05})$$

Because there is a small amount of absorption at the wavelength of the wavelength $\lambda_{100}$ obtained in this way, a wavelength $\lambda_{200}$, at which there is almost no absorption, is obtained by adding $(4/15) \times (\lambda_{80} - \lambda_{05})$ to wavelength $\lambda_{100}$ as a margin. That is, $$\lambda_{200} = \lambda_{80} + (4/15) \times (\lambda_{80} - \lambda_{05}) + (4/15) \times (\lambda_{80} - \lambda_{05})$$
$$= \lambda_{80} + (8/15) \times (\lambda_{80} - \lambda_{05})$$

In order to ensure that this wavelength $\lambda_{200}$ be smaller than the wavelength $\lambda_{ex}$ of the stimulating light (that is, so that $\lambda_{200} < \lambda_{ex}$), the aforementioned emitting of fluorescent light by the aforementioned optical element when it is irradiated by stimulating light can be controlled by selecting optical element materials having the desired properties.

Note that, as shown by the broken line in FIG. 3, the endoscope front-end portion 40, including a portion of light guide 13, projecting lens 14, objective lens 21 and a portion of image fiber 22 is inserted into the body when examination of the living-tissue subject thereof is performed.

Next, the operation of the first fluorescent endoscope according to the first embodiment will be explained.

The stimulating light Le emitted from stimulating light source 11 passes through condensing lens 12, light guide 13 and projecting lens 14 and is projected onto living-tissue subject 1. The autofluorescent light Fj emitted by living-tissue subject 1 upon irradiation thereof by stimulating light Le is focused by objective lens 21 onto input face 22a of image fiber 22 as an autofluorescent image Zj, and is propagated to the output face 22b of image fiber 22 at the other end thereof. The autofluorescent image Zj propagated to output face 22b of image fiber 22 is focused on the light-receiving face of photographing element 31 by relay lens 23a and relay lens 23b, however, along this optical path, a specified range of frequencies of the autofluorescent light Lj is extracted by dichroic mirror 24, and the autofluorescent light Lj irradiated to the side of and near to each of the light receiving pixels of photographing element 31 is condensed onto each light-receiving pixel by micro lens array 26 and split for each pixel by mosaic filter 27.

Here, the relationship between the strength of the autofluorescent light Lj emitted by living-tissue subject 1 that has arrived at the light-receiving face of photographing element 31 and the strength of the fluorescent light Lk emitted from optical element 20 when reflected stimulating light Lh passes therethrough will be explained.

If the value of the strength per unit area at the light-receiving face of photographing element 31 of the autofluorescent light Lj that has been emitted by the normal tissue of a living-tissue subject 1 located at a far-point, has been propagated within optical element 20 and has arrived at the light-receiving face of photographing element 31 is designated as 100; the strength per unit area at the light-receiving face of photographing element 31 of the autofluorescent light Lj that has been emitted by the cancerous tissue of a living-tissue subject 1 located at a far-point and propagated within optical element 20 to arrive at the light-receiving face of photographing element 31 is 10, and because the strength per unit area at the light-receiving face of photographing element 31 of the fluorescent light Lk emitted from optical element 20 when reflected stimulating light Lh that has been reflected from a living-tissue subject located at a close-position passes therethrough is 1 or less, the strength of the fluorescent light Lk, which becomes mixed with the autofluorescent light Lj as noise, can be controlled to be a low strength, and even under the aforementioned condition of the observational limit, a fluorescent image Zj in which it is possible to clearly distinguish the difference between normal tissue and cancerous tissue can be photographed by use of photographing element 31.

That is to say, even if the components forming optical element 20 which are in front of stimulating light cutoff filter 25, including objective lens 21, into which the reflected stimulating light is emitted, image fiber 22, relay lens 23a, dichroic mirror 24 and relay mirror 23b propagate the reflected stimulating light Lh, by disposing a stimulating light cutoff filter 25 in front of micro lens array 26 and mosaic filter 27, the strength of the fluorescent light Lk received by the photographing element can be reduced.

Figure 4:
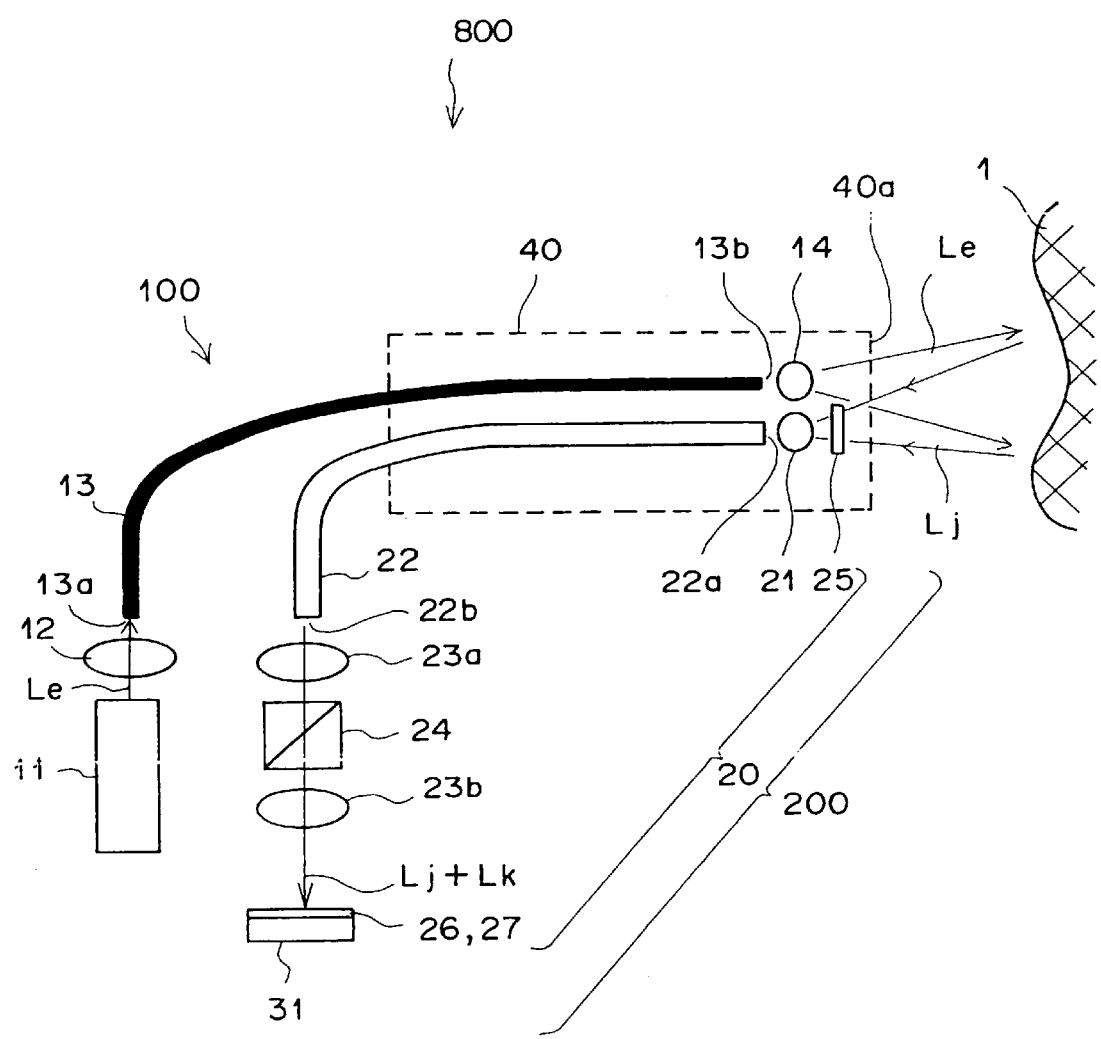
FIG. 4 is a schematic drawing of the configuration of a fiber-optic endoscope according to the second embodiment of the present invention.

FIG. 4 is a schematic drawing of a fiber optic endoscope according to the second embodiment of the present invention, and structures shown therein that have the same functions as those of the first embodiment are labeled with the same reference numerals.

As shown in FIG. 4, according to the fiber-optic endoscope apparatus 800 of the second embodiment, the stimulating light cutoff filter 25 that was disposed between the output face of the image fiber and the photographing element in the first embodiment has been moved to the input side of objective lens 21, that is to say, the fiber-optic endoscope apparatus 800 of the second embodiment has an optical element 20 disposed further forward than the objective lens on the side at which the autofluorescent light Lj enters. The other structures are the same as those of the first embodiment.

Therefore, the material used to form the optical element 20 is selected so that the relationship of the average strength of the autofluorescent light Fj emitted by the normal tissue of living-tissue subject 1 upon irradiation thereof by stimulating light Le and which has been passed through optical element 20 and received by photographing element 31, that is normal tissue fluorescent light strength K, to the average strength of the fluorescent light emitted by the constituent material of optical element 20 upon stimulation thereof by the reflected stimulating light Lf reflected by the living-tissue subject caused when said reflected stimulating light Lf passes therethrough, that is optical element fluorescent light strength B satisfied the condition expressed by the formula: $K \geq B \times 10^4$.

Next, the operation of the fiber-optic endoscope apparatus 800 of the second embodiment will be explained.

The stimulating light Le emitted from stimulating light source 11 passes through condensing lens 12, light guide 13 and projecting lens 14, and is projected onto living-tissue subject 1. The autofluorescent light Fj emitted by living-tissue subject 1 upon irradiation thereof by stimulating light Le passes through stimulating light cutoff filter 25 and is focused by objective lens 21 onto input face 22a of image fiber 22 as an autofluorescent image Zj, which then passes through image fiber 22, relay lens 23a, dichroic mirror 24, relay lens 23b, micro lens array 26 and mosaic filter 27, and is focused on the light-receiving face of photographing element 31. Then, the autofluorescent image Zj focused on the light-receiving face of photographing element 31 is photographed by said photographing element 31.

Here, the relationship between the strength of the autofluorescent light Lj emitted by living-tissue subject 1 that has arrived at the light-receiving face of photographing element 31 and the strength of the fluorescent light Lk emitted from optical element 20 when reflected stimulating light Lh passes therethrough will be explained.

In the same way as in the first embodiment, if the value of the strength per unit area at the light-receiving face of photographing element 31 of the autofluorescent light Lj that has been emitted by the normal tissue of a living-tissue subject 1 located at a far-point, has been propagated within optical element 20 and has arrived at the light-receiving face of photographing element 31 is designated as 100; the strength per unit area at the light-receiving face of photographing element 31 of the autofluorescent light Lj that has been emitted by the cancerous tissue of a living-tissue subject 1 located at a far-point and propagated within optical element 20 to arrive at the light-receiving face of photographing element 31 is 10, and because the strength per unit area at the light-receiving face of photographing element 31 of the fluorescent light Lk emitted from optical element 20 when reflected stimulating light Lh that has been reflected from a living-tissue subject located at a close-position passes therethrough is 1 or less, the strength of the fluorescent light Lk, which becomes mixed with the autofluorescent light Lj as noise, can be controlled to be a low strength, and even under aforementioned condition of the observational limit, a fluorescent image Zj in which it is possible to clearly distinguish the difference between normal tissue and cancerous tissue can be photographed by use of photographing element 31.

That is to say, by disposing stimulating light cutoff filter 25 at the first position at which the autofluorescent light Lj enters into optical element 20, the strength of the fluorescent light Lk emitted from the components constituting the optical element 20 on the other side of stimulating light cutoff filter 25, which include objective lens 21, image fiber 22, relay lens 23a, dichroic mirror 24, relay lens 23b, micro lens array 26 and mosaic filter 27, and received by photographing element 31 can be reduced.

Figure 5:
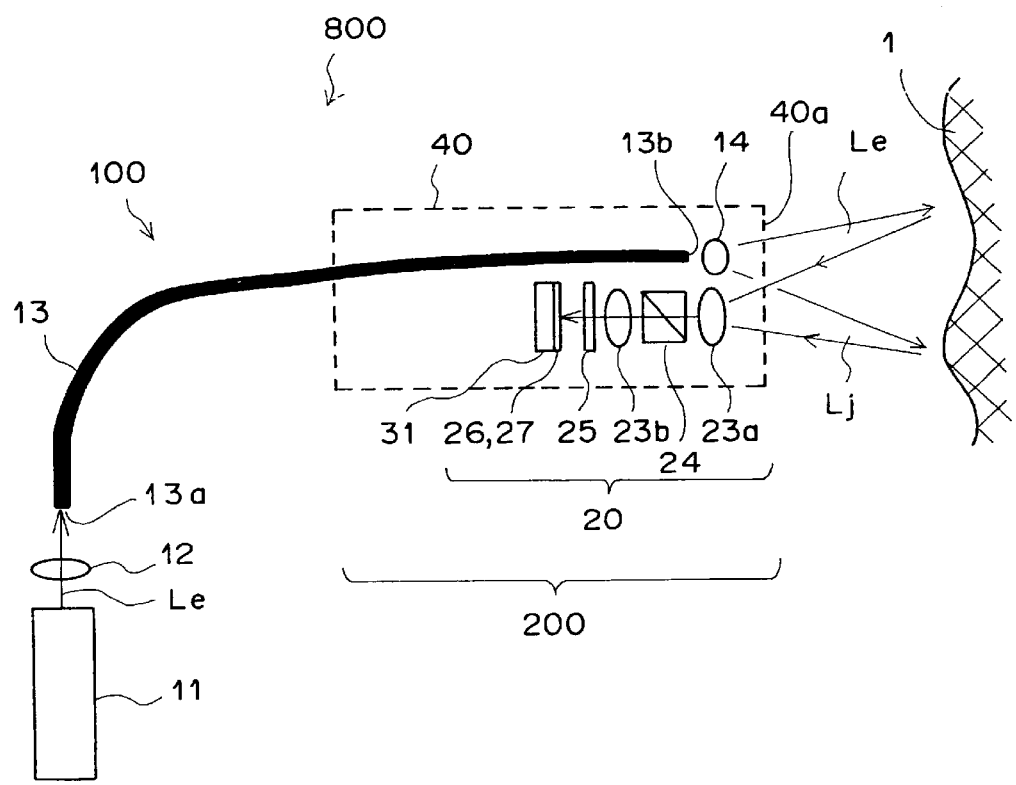
FIG. 5 is a schematic drawing of the configuration of an electron endoscope according to the third embodiment of the present invention.

FIG. 5 is a schematic drawing of an electron endoscope according to the third embodiment of the present invention, and structures shown therein that have the same functions as those of the first embodiment are labeled with the same reference numerals.

As shown in FIG. 5, according to the electron endoscope apparatus 800 of the third embodiment, the objective lens 21 and the image fiber 22 employed in the first embodiment have been removed, and relay lens 23a, dichroic mirror 24 relay lens 23b, stimulating light cutoff filter 25, micro lens array 26, mosaic filter 27 and photographing element 31 are mounted inside the endoscope front-portion 40. The other structures are the same as those of the first embodiment.

Note that the material used for forming the optical element 20 is selected so as to satisfy the condition expressed by the formula: $K \geq B \times 10^4$.

Next, the operation of the electron endoscope apparatus 800 according to the third embodiment will be explained.

The stimulating light Le emitted from stimulating light source 11 passes through condensing lens 12, light guide 13 and projecting lens 14, and is projected onto living-tissue subject 1. The autofluorescent light Fj emitted by living-tissue subject 1 upon irradiation thereof by stimulating light Le passes through relay lens 23a, dichroic mirror 24, relay lens 23b, stimulating light cutoff filter 25, micro lens array 26 and mosaic filter 27, and is focused on the light-receiving face of photographing element 31. Then, the autofluorescent image Zj focused on the light-receiving face of photographing element 31 is photographed by said photographing element 31.

Here, the relationship between the strength of the autofluorescent light Lj emitted by living-tissue subject 1 that has arrived at the light-receiving face of photographing element 31 and the strength of the fluorescent light Lk emitted from optical element 20 when reflected stimulating light Lh passes therethrough will be explained.

In the same way as in the first embodiment, if the value of the strength per unit area at the light-receiving face of photographing element 31 of the autofluorescent light Lj that has been emitted by the normal tissue of a living-tissue subject 1 located at a far-point, has been propagated within optical element 20 and has arrived at the light-receiving face of photographing element 31 is designated as 100; the strength per unit area at the light-receiving face of photographing element 31 of the autofluorescent light Lj that has been emitted by the cancerous tissue of a living-tissue subject 1 located at a far-point and propagated within optical element 20 to arrive at the light-receiving face of photographing element 31 is 10, and because the strength per unit area at the light-receiving face of photographing element 31 of the fluorescent light Lk emitted from optical element 20 when reflected stimulating light Lh that has been reflected from a living-tissue subject located at a close-position passes therethrough is 1 or less, the strength of the fluorescent light Lk, which becomes mixed with the autofluorescent light Lj as noise, can be controlled to be a low strength, and even under aforementioned condition of the observational limit, a fluorescent image Zj in which it is possible to clearly distinguish the difference between normal tissue and cancerous tissue can be photographed by use of photographing element 31.

Note that, according to the embodiment described above, an explanation was preferred based mainly on an example of diagnosing a cancerous tissue, however, the fluorescent endoscopes according to the present invention can be applied as a diagnostic apparatus for distinguishing tissues afflicted with diseases other than cancer.

As described above, according to the present invention, by reducing the emission of the fluorescent light, which becomes noise, emitted from the optical element that propagates the autofluorescent light emitted from a living tissue subject, the difference between normal tissue and diseased tissue can be clearly distinguished.

What is claimed is:

1. A fluorescent endoscope apparatus comprising a stimulating light projecting means for irradiating a living-tissue subject with stimulating light, and a photographing means formed of an optical element for transferring the autofluorescent light emitted from the live-subject tissue upon irradiation thereof by stimulating light and a photographing element for photographing the autofluorescent light transferred thereto by said optical element, wherein:

said optical element is constructed so that the relationship of the normal-tissue fluorescent light of a strength K, which is the strength of the autofluorescent light emitted from the normal tissue of the live-tissue subject that has been transferred through said optical element and received by the photographing element, to the optical-element fluorescent light of a strength B, which is the strength of the fluorescent light emitted by said optical element when the reflected stimulating light reflected from the living tissue subject upon irradiation thereof by stimulating light is propagated through said optical element, satisfies the condition expressed by the formula: $K \geq B \times 10^4$;

said photographing element is provided with a stimulating light cutoff filter for selectively cutting off said stimulating light;

said stimulating light cutoff filter is provided with a panel of optical glass and a multiple layer dielectric film formed thereon;

said optical element comprises a plurality of optical element components; and wherein said multiple-layer dielectric film and at least one of said optical element components through which the autofluorescent light is passed and which is disposed between said multiple-layer dielectric film and the living-tissue subject has properties satisfying the condition expressed by the following formulae:

$$\lambda_{ex} > \lambda_{80} + (8/15) \times (\lambda_{80} - \lambda_{05})$$

Where:
   $\lambda_{ex}$=the wavelength of the stimulating light
   $\lambda_{80}$=the wavelength at which the optical element exhibits the transmittance of 80%
   $\lambda_{05}$=the wavelength at which the optical element exhibits the transmittance of 5%.

2. The fluorescent endoscope apparatus as defined in claim 1, wherein said stimulating light has a wavelength of 445 nm or smaller.

3. The fluorescent endoscope apparatus as defined in claim 2, wherein the stimulating light source comprises one of a GaN semiconductor laser, a mercury lamp, a xenon lamp, and a metal halide lamp.

* * * * *